United States Patent
Sengupta et al.

(10) Patent No.: US 8,328,724 B2
(45) Date of Patent: Dec. 11, 2012

(54) METHOD FOR IMAGING INTRACAVITARY BLOOD FLOW PATTERNS

(75) Inventors: Partho P. Sengupta, Rochester, MN (US); Marek Belohlavek, Scottdale, AZ (US); Bijoy K. Khandheria, Fountain Hills, AZ (US)

(73) Assignee: MAYO Foundation For Medical Education and Research, Rochester, MN (US)

(*) Notice: Subject to any disclaimer, the term of this patent is extended or adjusted under 35 U.S.C. 154(b) by 449 days.

(21) Appl. No.: 12/298,222

(22) PCT Filed: May 8, 2007

(86) PCT No.: PCT/US2007/011205
§ 371 (c)(1),
(2), (4) Date: Oct. 23, 2008

(87) PCT Pub. No.: WO2007/136554
PCT Pub. Date: Nov. 29, 2007

(65) Prior Publication Data
US 2009/0187100 A1  Jul. 23, 2009

Related U.S. Application Data

(60) Provisional application No. 60/800,369, filed on May 15, 2006.

(51) Int. Cl.
*A61B 8/00* (2006.01)

(52) U.S. Cl. ........ 600/458; 600/437; 600/439; 600/443; 600/447; 600/453; 600/454; 600/459

(58) Field of Classification Search ............. 600/431, 600/437, 441, 450, 453, 458
See application file for complete search history.

(56) References Cited

U.S. PATENT DOCUMENTS

| | | | |
|---|---|---|---|
| 5,285,788 A | 2/1994 | Arenson et al. | |
| 5,797,396 A | 8/1998 | Geiser et al. | |
| 6,080,107 A * | 6/2000 | Poland | 600/458 |
| 6,086,540 A * | 7/2000 | Bonneville et al. | 600/458 |
| 6,352,509 B1 * | 3/2002 | Kawagishi et al. | 600/443 |
| 6,719,697 B2 * | 4/2004 | Li | 600/454 |
| 2002/0151794 A1 * | 10/2002 | Li | 600/454 |
| 2003/0012735 A1 | 1/2003 | Unger et al. | |
| 2003/0229285 A1 | 12/2003 | Simpson et al. | |
| 2006/0051297 A1 | 3/2006 | Schneider et al. | |
| 2006/0078501 A1 | 4/2006 | Goertz et al. | |
| 2007/0162080 A1 * | 7/2007 | Brockway et al. | 607/17 |
| 2007/0167809 A1 * | 7/2007 | Dala-Krishna | 600/459 |
| 2007/0238954 A1 * | 10/2007 | White et al. | 600/407 |

OTHER PUBLICATIONS

The International Search Report and Written Opinion corresponding to PCT/US2007/011205 with a mailing date of Oct. 24, 2007.

* cited by examiner

*Primary Examiner* — Tse Chen
*Assistant Examiner* — Baisakhi Roy
(74) *Attorney, Agent, or Firm* — Quarles & Brady, LLP

(57) ABSTRACT

Heart diseases are detected by producing a series of ultrasound images that depict the blood flow pattern in the left ventricle at successive phases of the cardiac cycle. The blood flow pattern images are produced by injecting a diluted contrast agent and tracking the contrast agent particles as they flow through the left ventricle by acquiring ultrasound images at a high frame rate.

20 Claims, 4 Drawing Sheets

METHOD FOR IMAGING INTRACAVITARY BLOOD FLOW PATTERNS

CROSS-REFERENCE TO RELATED APPLICATIONS

This application claims the benefit of U.S. Provisional patent application Ser. No. 60/800,369 filed on May 15, 2006 and entitled "Method For Imaging Intracavitary Blood Flow Patterns".

STATEMENT REGARDING FEDERALLY SPONSORED RESEARCH

This invention was made with government support under Grant No. HL 70363 and Grant No. HL068573, awarded by the National Institute of Health and, in part, by Grant No. HL 6855 from the National Institute of Health. The United States Government has certain rights in this invention.

BACKGROUND OF THE INVENTION

The field of the invention is coherent imaging using vibratory energy, such as ultrasound and, in particular, ultrasound imaging of the heart.

There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode). The present invention relates to a backscatter method for producing ultrasound images.

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object, and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed. The so-called "M-scan" is very similar to the B-scan in that it is a continuous series of B-scans. This mode is commonly used to show motion of the heart so that heart structures can be observed during all phases of the cardiac cycle.

Ultrasonic transducers for medical applications are constructed from one or more piezoelectric elements sandwiched between a pair of electrodes. When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio.

A primary problem in ultrasonic imaging has been that many of the body's internal structures have similar characteristics as regards the reflection of ultrasonic energy, so that it is difficult to obtain as clear and detailed images of many of the structures as is desired. In particular, many of the structures of interest, such as the muscles of the heart, are perfused with blood, so that it is difficult to distinguish between blood vessels and the chambers of the heart and the heart muscles.

One solution to this problem has been ultrasonic imaging using contrast agents injected into the blood stream. Ultrasonic contrast agents are now commercially available and are essentially small bubbles of gas, such as air, formed by agitating a liquid or bubbling gas through a liquid, such as a saline solution or a solution containing a bubble forming compound, such as albumin. When insonicated, the bubbles resonate at their resonant frequency and emit energy at both the fundamental and second harmonic of their resonant frequency, thereby returning an enhanced signal at or around these frequencies and thereby providing an enhanced image of the liquid or tissue containing the contrast agent. It is also well known that the bubbles "disappear" when insonicated and the current theory is that the insonication ruptures the bubble's shell, thereby allowing the gas to dissipate into the surrounding liquid or tissue.

The use of ultrasonic contrast agents is thereby advantageous in allowing enhanced imaging using ultrasonics rather than x-rays, thereby eliminating the radiation hazard and allowing the use of equipment that is significantly less expensive and hazardous to use. Also, the agents are non-toxic and dissolve relatively quickly into waste products, such as air and albumin, that are normally found in the body and that are themselves non-toxic. Further, the insonication of the agent in itself destroys the agent, so that the agent can effectively be "erased" during the imaging process to a degree.

The left ventricle (LV) in a mammalian heart carries out the functions of suction and ejection, transiting functionally through short-lived phases known as isovolumic intervals. Ventricular disease or disturbed myocardial electrical activation primarily prolongs the isovolumic intervals, with either no significant change or a shortening of ejection and filling times.

At the cellular level, the isovolumic intervals are associated with active fluxes in myoplasmic and sarcolemmal calcium that either initiate or reverse interactions between cardiac myofilaments. At the tissue level, isovolumic intervals are associated with asynchronous but synergistic movements of the subendocardial and subepicardial regions. During isovolumic contraction (IVC), the subendocardial fibers that form a right-handed helix shorten, while the left-handed helically oriented subepicardial fibers lengthen simultaneously. Conversely, during isovolumic relaxation (IVR), the subepicardial fibers that form the left-handed helix lengthen, while the right-handed helically directed subendocardial fibers shorten briefly. An initial asymmetric deformation of the LV may represent a "flow-directing feature" of the myocardial wall mechanics that reverses the direction of blood flow.

Conventionally, the timing of mitral valve closure has been used for dividing the preejection period into 2 component intervals. The first component, also referred to as "electromechanical delay," is in continuity with end-diastole and refers to the interval from the onset of the Q wave on surface electrocardiography to mitral valve closure. Isovolumic contraction is the period that follows mitral valve closure and is characterized by a rapid rise in LV pressure before opening of the aortic valve. Recent observations indicate that cardiac muscle shortening is initiated significantly before closure of the mitral valve. Whether blood flow during this early stage accelerates into an axial momentum that ultimately causes mitral valve closure remains unclear. This necessitates further clarification on the rheologic features and nature of LV performance during the preejection period.

Previous investigations have used echocardiography and magnetic resonance velocity mapping of blood circulation for deciphering the features of LV intracavitary blood flow patterns. An intriguing aspect of this flow is the occurrence of intracavitary vortices. Findings from in vitro experiments suggested that strong vortices are required at the onset of ventricular contraction near the LV outflow, and that without these vortices, the mitral valve would remain open at the onset of ventricular contraction. However, features of intracavitary flow visualized directly in vivo during isovolumic periods have remained a mystery. Time-resolved flow vector quantifications could provide insights into why the initial LV deformations are asymmetric.

SUMMARY OF THE INVENTION

The present invention is a method for acquiring in vivo images of the heart that enable its operation to be analyzed.

More specifically, a contrast agent is administered to the subject and as the contrast agent particles flow through a subject cardiac chamber, ultrasound images are acquired at a high frame rate (high temporal resolution). The echo signals are processed by a particle tracking processor to produce images that depict the pattern of particle flow through the heart chamber.

Generally, the present invention is directed to visualizing blood flow in vivo within cardiac cavities or within blood vessels by using injected particles (such as microbubbles) that act as blood tracers and are visualized by high-temporal resolution ultrasound imaging.

The present invention is able to determine, for example, patterns of isovolumic intracardiac flow that could assist in diagnosing heart diseases. As another example, the present invention can determine whether electromechanical interventions that alter the mechanical events during a cardiac cycle also alter features of flow during the preejection period and lead to changes in the timing of mitral valve and aortic valve opening and closing. Such information indicates whether or not pacing should be employed and how it should be employed. Heart failure is a growing problem all over the world, and the emergence of cardiac resynchronization therapy in treating heart failure has renewed interest in understanding the electromechanical activation sequence of mammalian hearts. Recent basic science and clinical studies have further reported an unfavorable proarrhythmic effect of epicardial pacing. The present invention acquires information indicating that a change in the electromechanical activation sequence by epicardial pacing from the LV base delays acceleration of redirected streams toward the LV outflow, delaying closure of the mitral valve and opening of the aortic valve. This argues against indiscriminate use of epicardial pacing, particularly from the basal region, in the absence of a clear transmural block that delays the spread of electrical activation to the epicardial region. Furthermore, the goals of resynchronization therapy may not be realized if the activation sequence is not carefully synchronized with the direction of blood flow. This may have relevance for the 20% to 30% of patients with heart failure who have no response to cardiac resynchronization therapy.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE INVENTION

Figure 1:
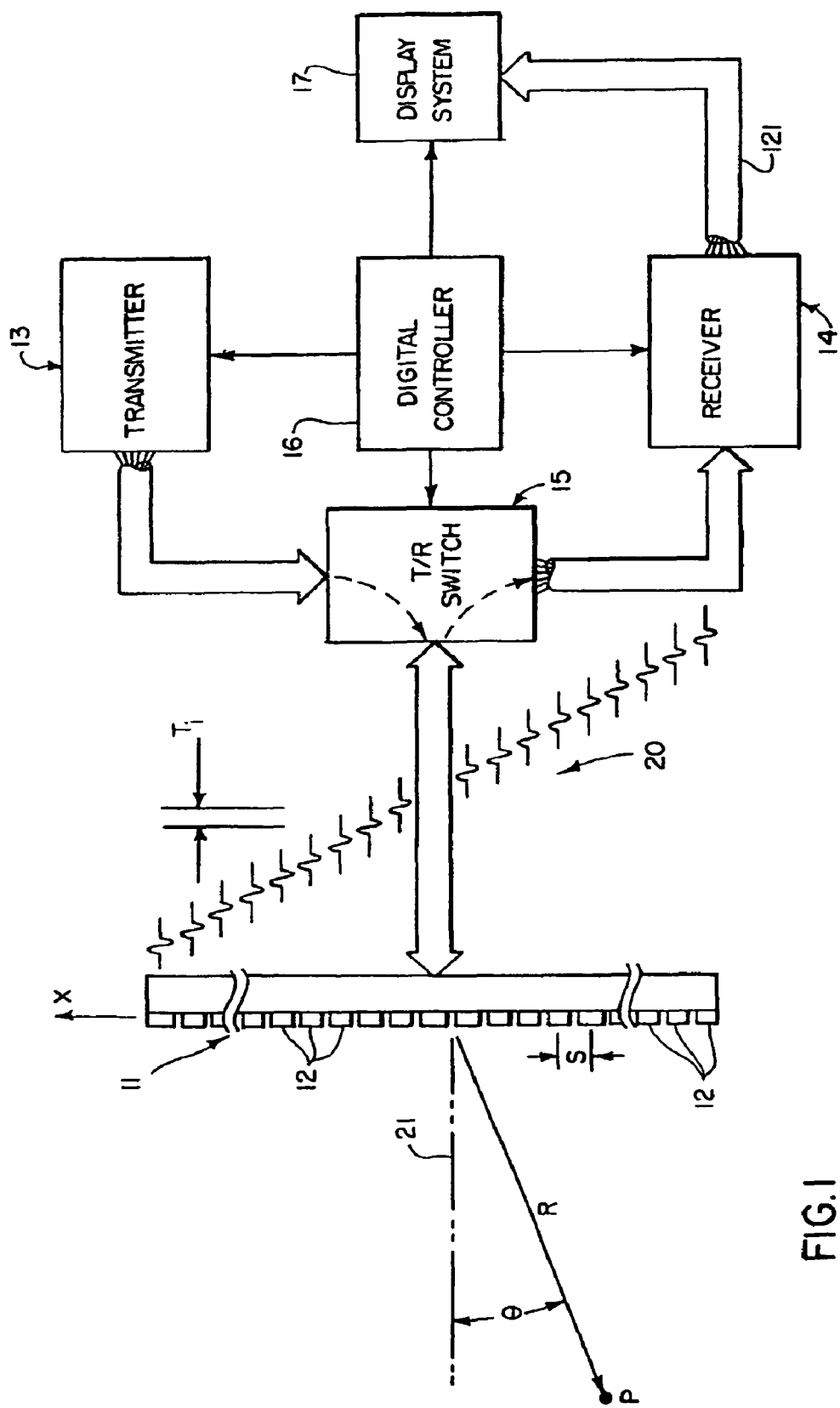
FIG. 1 is a block diagram of an ultrasonic imaging system that employs the present invention.

Referring particularly to FIG. 1, an ultrasonic imaging system includes a transducer array 11 comprised of a plurality of separately driven elements 12 that each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal that is employed to produce a line in an image on a display system 17.

The transmitter 13 drives the transducer array 11 such that the ultrasonic energy produced is directed, or steered, in a beam. A B-scan can therefore be performed by moving this beam through a set of angles from point-to-point rather than physically moving the transducer array 11. To accomplish this, the transmitter 13 imparts a time delay ($T_i$) to the respective pulses 20 that are applied to successive transducer elements 12. If the time delay is zero ($T_i$=0), all the transducer elements 12 are energized simultaneously and the resulting ultrasonic beam is directed along an axis 21 normal to the transducer face and originating from the center of the transducer array 11. As the time delay ($T_i$) is increased as illustrated in FIG. 1, the ultrasonic beam is directed downward from the central axis 21 by an angle θ. A sector scan is performed by progressively changing the time delays $T_i$ in successive excitations. The angle θ is thus changed in increments to steer the transmitted beam in a succession of directions.

Referring still to FIG. 1, the echo signals produced by each burst of ultrasonic energy emanate from reflecting objects located at successive positions (R) along the ultrasonic beam. These are sensed separately by each segment 12 of the transducer array 11 and a sample of the magnitude of the echo signal at a particular point in time represents the amount of reflection occurring at a specific range (R). Due to the differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal that accurately indicates the total ultrasonic energy reflected from each focal point P located at range R along the ultrasonic beam oriented at the angle θ.

To simultaneously sum the electrical signals produced by the echoes from each transducer element 12, time delays are introduced into each separate transducer element channel of the receiver 14. In the case of the linear array 11, the delay introduced in each channel may be divided into two components, one component is referred to as a beam steering time delay, and the other component is referred to as a beam focusing time delay. The beam steering and beam focusing time delays for reception are precisely the same delays ($T_i$) as the transmission delays described above. However, the focusing time delay component introduced into each receiver channel is continuously changing during reception of the echo to provide dynamic focusing of the received beam at the range R from which the echo signal emanates.

Under the direction of the digital controller 16, the receiver 14 provides delays during the scan such that the steering of the receiver 14 tracks with the direction of the beam steered by the transmitter 13, and it samples the echo signals at a succession of ranges and provides the proper delays to dynamically focus at points P along the beam. Thus, each emission of an ultrasonic pulse results in the acquisition of a series of data points that represent the amount of reflected sound from a corresponding series of points P located along the ultrasonic beam.

The display system 17 receives the series of data points produced by the receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display.

Figure 2:
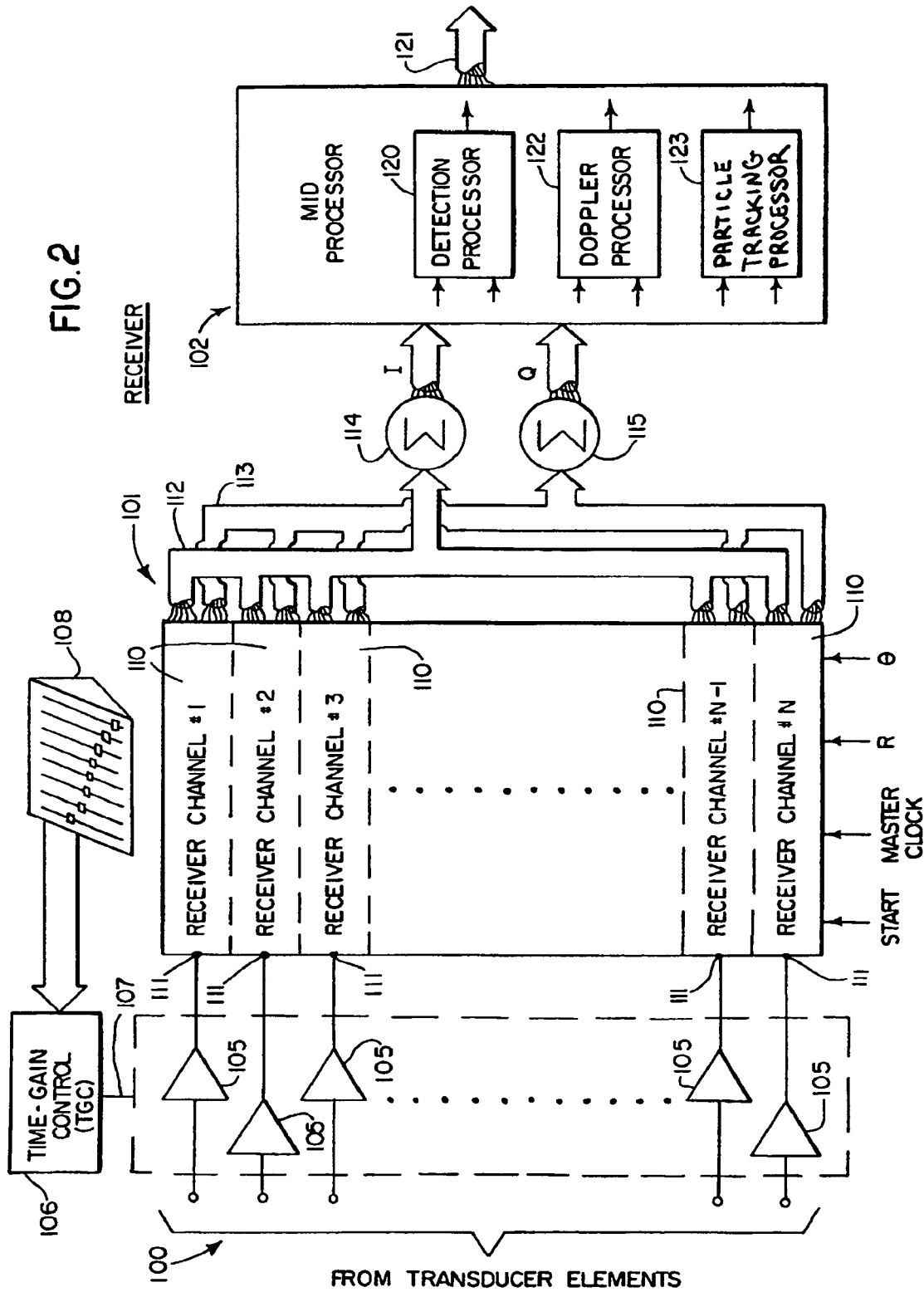
FIG. 2 a block diagram of a receiver that forms part of the system of FIG. 1.

Referring particularly to FIG. 2, the receiver 14 is comprised of three sections: a time-gain control section 100, a beam forming section 101, and a mid processor 102. The time-gain control section 100 includes an amplifier 105 for each of, for example, N=128 receiver channels and a time-gain control circuit 106. It is noted that 128 receiver channels is selected for exemplary purposes and that other numbers of channels are contemplated. The input of each amplifier 105 is connected to a respective one of the transducer elements 12 to receive and amplify the echo signal that it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) time gain compensation (TGC) linear potentiometers 108 to values that provide a relatively uniform brightness over the entire range of the sector scan. The time interval over which the echo signal is acquired determines the range from which it emanates, and this time interval is divided into eight segments by the TGC control circuit 106. The settings of the eight potentiometers are employed to set the gain of the amplifiers 105 during each of the eight respective time intervals so that the echo signal is amplified in ever increasing amounts over the acquisition time interval.

The beam forming section 101 of the receiver 14 includes separate receiver channels 110. Each receiver channel 110 receives the analog echo signal from one of the TGC amplifiers 105 at an input 111, and it produces a stream of digitized output values on an "I" bus 112 and a "Q" bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam (θ).

Referring still to FIG. 2, the mid processor section 102 receives the beam samples from the summing points 114 and 115. The "I" and "Q" values of each beam sample is a 16-bit digital number that represents the in-phase and quadrature components of the magnitude of the reflected sound from a point (R, θ). The mid processor 102 can perform a variety of calculations on these beam samples, where choice is determined by the type of image to be reconstructed. For example, if a conventional magnitude image is to be produced, a detection process indicated at 120 is implemented in which a digital magnitude M is calculated from each beam sample and output at 121.

$$M=\sqrt{I^2+Q^2}$$

The mid processor may also include a Doppler processor 112 such as that described in U.S. Pat. No. 4,217,909 issued on Aug. 19, 1980 and entitled "Directional Detection of Blood Velocities In An Ultrasound System"; or such as that described in U.S. Pat. No. 4,265,126 issued on May 5, 1981 and entitled "Measurement of True Blood Velocity By an Ultrasound System". Such Doppler processors often employ the phase information (φ) contained in each beam sample to determine the velocity of reflecting objects along the direction of the beam (i.e. radial direction from the center of the transducer 11, where $$\phi=\tan^{-1}(I/Q).$$

The mid processor 102 also includes a particle tracking processor 123. The particle tracking processor 123 is similar to what is referred to in the art as particle image velocimetry ("PIV"). In this application, the particle tracking processor detects the microbubble contrast agent particles by their characteristic acoustic signature in successive image frames and calculates therefrom their displacement vector and velocity. Other quantitative blood flow parameters such as acceleration, vorticity, turbulence, circulation, and laminarity are also calculated for each image frame. Any of these flow parameters may be output to the display where they are shown in color superimposed over an anatomic, magnitude image of the structure being imaged.

The particle tracking processor 123 uses pairs of sequential digital images for calculating the direction and magnitude of particle flow. Displacement of the particles in the second image, relative to the position of the particles in the first image, is a measure of the motion of the fluid. In some embodiments images are analyzed using a cross-correlation interrogation algorithm combined with fast Fourier transformation (INSIGHT; TSI Inc., Shoreview, Minn.). The interrogation spot size is 32×32 pixels with 50% overlap. Maximal particle displacement is less than 5 pixels. With this setup, we avoid a substantial loss of particle pairs. The deformation grid engine is used, because of high-velocity gradients in the flow, to increase the amount of information extracted from the images. This algorithm deforms the grid according to the previous vector field results; hence, all particle displacements within an interrogation spot are at the same location after the deformation is performed. The first processing calculates the vector displacement using cross-correlation with or without interrogation spot offset. The second processing pass offsets the spots for the integer pixel value, found during the first pass, in the region of high-velocity gradients. In the third pass, the 4 neighboring vectors in the spot corners were used to deform the spot. This method helps restore elongated and splintered peaks to a Gaussian appearance and creates a more accurate flow field with more good vectors than in a regular, underformed grid. To find sub-pixel displacement, we used 3 points, 2 directions, and 1-dimensional Gaussian peak fitting.

The result is a series of images that reveal how the microbubble particles flow through the left ventricle during successive phases of the cardiac cycle, plus the ability to calculate flow parameters at locations within the left ventricle and either display such flow parameters or use them in subsequent diagnostic steps as described below.

Figure 3:
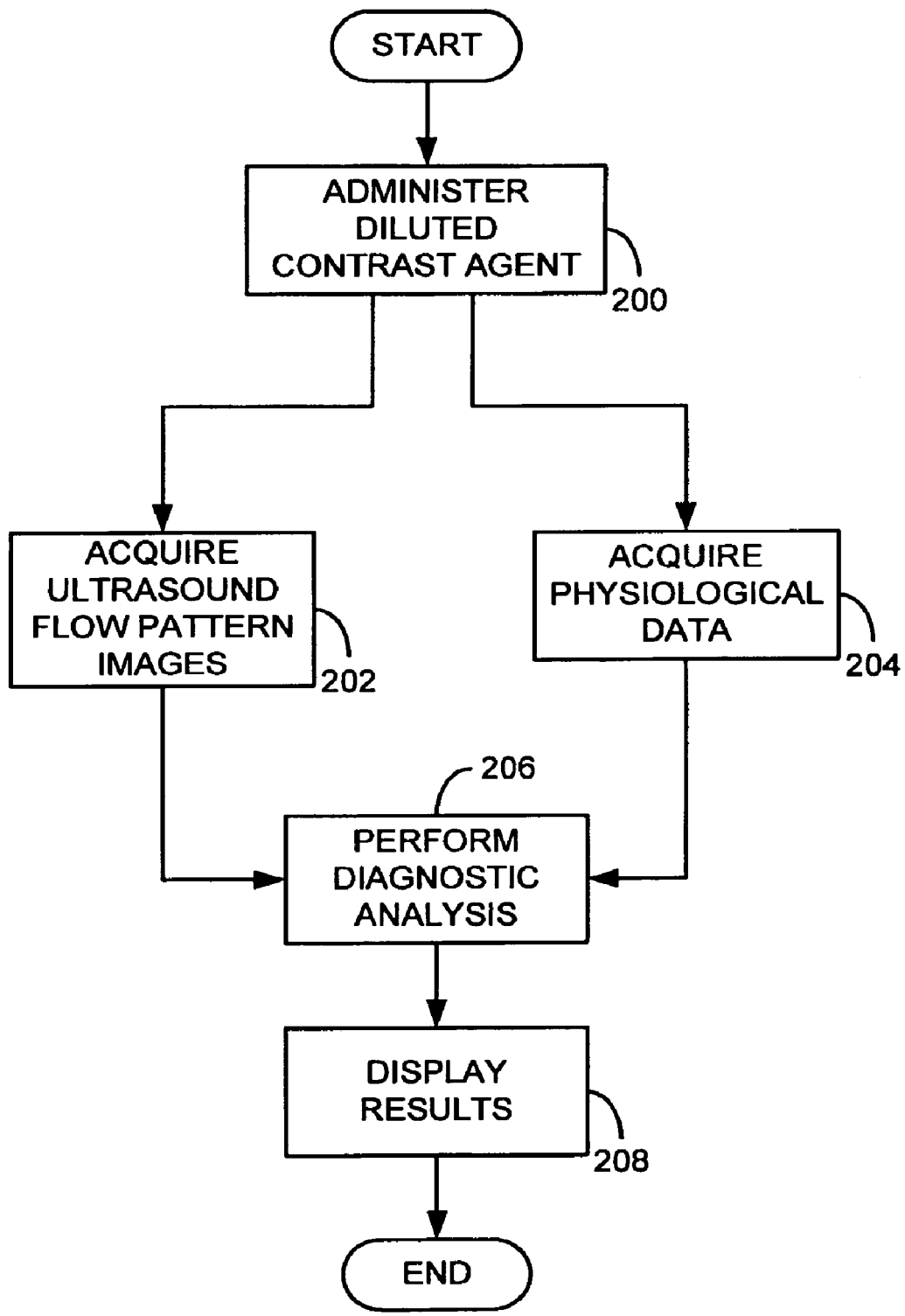
FIG. 3 is a flow chart of a method for diagnosing cardiac diseases using the system of FIG. 1.

Referring particularly to FIG. 3, the ultrasound system may be used to provide unique information that is used to diagnose a number of different diseases of the heart. As indicated at process block 200, the first step in the diagnostic process is to administer a contrast agent to the subject. A perfluoropropane gas-filled, lipid-stabilized microbubble contrast agent such as that sold by Bristol-Myers Squibb Medical Imaging, Inc. under the trademark "Definity" is used, and it is administered intravenously in either of two ways. However, it is noted that other existing or future contrast agents could be usable in a similar way. A bolus injection of 10 micrograms/kg of subject body weight is administered, or an infusion of 1 mL dissolved in 100 mL/min of saline at a rate of around 0.01-0.05 mL/min is administered. The important factor is that the contrast microbubbles are administered in a much diluted form when compared to their injection for the usual purpose of contrast enhancement. In this application the microbubbles serve as trackable particles that flow with the blood to reveal the blood flow patterns. They produce a strong and unique sonic signature that makes tracking them easier.

As indicated at process block 202, the next step is to acquire ultrasound parameter images using the above-described ultrasound system. When imaging the left ventricle, image acquisition should begin a few cardiac cycles after bolus injection of contrast microbubbles or after the infusion of contrast microbubbles reaches a continuous rate. The microbubbles should appear as individual scatterers in the anatomical magnitude images that are produced by the ultrasound system.

There are a number of factors that facilitate acquisition of parameter images. A broadband transducer 11 is used with approximately 1.7 MHz fundamental and 3.4 MHz harmonic frequency. The scan sector can be narrow to capture the entire flow field in the left ventricle, but the heart walls can be excluded. An important factor is that the rate at which image frames are acquired is very high in order to enable successful particle tracking. A frame rate over 200 frames/sec has been found to be adequate when tracking microbubbles.

Ultrasound system settings that will optimize particle tracking include:

Harmonic or other mode optimized by the commercial vendor for high temporal and spatial resolution imaging of dissolved microbubbles;

Low mechanical index (<0.3);

Narrow scanning sector;

High frame rate (>200 frames/sec);

Focal point within or beneath the region with bubbles to achieve best tradeoff between particle survival and sharp depiction;

Maximal dynamic range; and

Temporal and spatial averaging (or persistence) should be switched off.

Referring still to FIG. 3, other physiological data may also be acquired from the subject as indicated by process block 204. This physiological data is acquired at the same time as the parameter images are acquired, and it may be time stamped such that the acquired physiological data can be temporally correlated with each parameter image frame. In some embodiments, the physiological data is ECG data, and the temporal correlation enables the flow patterns revealed by the parameter images to be correlated with the electrical signals produced in the heart during a cardiac cycle.

The acquired image frames are processed as described above to produce a number of different parametric image frames that are displayed along with the anatomic, magnitude image frames. In addition, the parametric image frames are stored and at the completion of the scan, these are transferred to a workstation where any one of a number of diagnostic analyses may be conducted as indicated at process block 206. Likewise, the acquired physiological data is input to the workstation where it may be employed in the analysis.

As will be described in detail below, many different diagnostic analyses may be performed using the parameter image frames and the results are reported and displayed as indicated at process block 208. Depending on the analysis performed, the results may include images in which a parameter such as kinetic energy, momentum, pressure gradient, velocity, acceleration, direction, vorticity, turbulence, and laminarity may be quantitatively displayed or overlaid on an anatomic image. In addition, a diagnosis may also be reported as discussed below.

Figure 4:
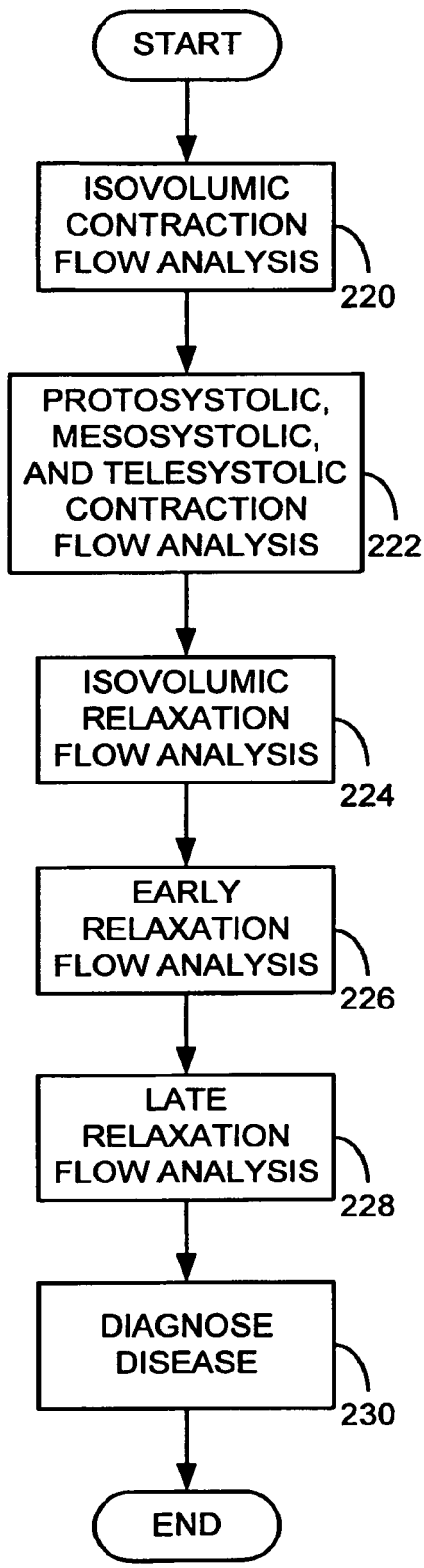
FIG. 4 is a flow chart of the steps used to diagnose heart diseases.

Referring particularly to FIG. 4, the diagnostic analysis of the acquired images for a number of heart diseases is performed by examining the images at successive phases of the cardiac cycle. In accordance with one embodiment of the present invention, analysis of the period of isovolumic contraction flow is indicated at 220. This period 220 extends from mitral valve closure to aortic valve opening, and it is characterized by redirection of blood flow from left ventricular apex to base and formation of a vortex across the inflow and the outflow regions of the left ventricular base. This is followed by an ejection phase that includes the protosystolic, mesosystolic and telesystolic contraction flow indicated at 222. The protosystolic phase is characterized by increasing left ventricular pressure and rapid acceleration of blood flow from left ventricle into aorta. Mesosystolic flow is characterized by pressure that plateaus, while flow continues from left ventricle into the aorta. The telesystolic period is characterized by a gradual fall of left ventricular pressure, before aortic valve closure. Blood flow decelerates during this phase. An isovolumic relaxation flow period follows as indicated at 224. This phase extends from aortic valve closure to mitral valve opening and is characterized by rapid base to apex redirection of blood flow followed by transient apex to base flow reversal. Next, an early relaxation flow phase occurs, as indicated at 226, that extends beyond mitral valve closure and is characterized by base to apex movement of flow across an open mitral valve. The early diastolic filling ends up with formation of a large vortex shed across the edge of an anterior mitral leaflet. The formation of vortex flow continues further during the period of diastasis under the mitral valve causing its transient inward movement. This is associated with equalization of left ventricular and atrial pressures. This transient halt in the rapid flow filling is also called diastasis. Multiple vortices can be seen inside the left ventricular cavity during this phase. And finally, a late relaxation flow phase indicated at 228. This phase follows the atrial wave signal as sensed on a surface ECG. This is characterized by a second phase of base to apex streaming of blood flow that ends with a vortex formation across the mitral valve and that continues smoothly into the isovolumic contraction phase. Based on an analysis of the parameter images at each of these cardiac phases, a diagnosis is made as indicated at 230.

Acute, Chronic Ischemia.

This disease is detected by unique flow characteristics that may occur in any one or more of the analysis phases. During the isovolumeric contraction flow phase 220, a change in vorticity and redirection of flow in the apical and affected regions may be detected. During the next analytical phase 222, turbulence, flow reversal or delayed flow redirection may occur near the ischemic myocardial region. Mitral valve regurgitation may be seen if ischemic valve insufficiency is present. During the isovolumic relaxation flow analysis phase 224, there may be a delayed time from the ECG R-wave indication to the onset of isovolumic relaxation flow. And finally, during the last two analysis phases 226 and 228, a slow early inflow of blood or turbulence around the mitral valve leaflets may be seen or the redirection of the flow may be delayed. Based on this analysis a report is generated by the diagnosis step 230 that indicates the severity of blood flow disturbance, the effectiveness of the work done by the heart and a prognosis regarding the chances for improvement after reperfusion of the damaged tissues.

Heart Failure.

This disease is also diagnosed by characteristic blood flow patterns in the left ventricle that occur in any one or more of the analysis phases. During the isovolumic contraction flow phase 220, chaotic blood flow redirection may occur, and during the next analysis phase 222, turbulent flow, poor directionality of flow towards the outflow may be seen. In addition, tracked stagnating red blood cells may occur. During the isovolumic relaxation flow phase 224, there may be a delayed time from the ECG R-wave indication to the onset of isovolumic relaxation flow. And during the last two analysis phases 226 and 228 slow inflow of blood or turbulence of inflowing blood through the mitral valve leaflets or delayed redirection of blood flow may occur. The diagnosis process 230 will indicate the severity, or stage, of ventricular failure and provide a disease outcome prognosis. Also, the effect of vasodilation therapy on the outcome is indicated.

Mitral Valve Regurgitation.

This disease is diagnosed by flow patterns that may be seen in four of the analysis phases. During the isovolumic contraction flow phase 220, an abrupt redirection of blood flow may be detected. During the analysis phase 222, regurgitant blood flow back into the left atrium through the mitral valve may be observed. And finally, during the early and late relaxation flow phases 226 and 228, rapid, voluminous inflow of blood into the left ventricle may be seen as well as turbulent blood flow around the mitral valve leaflets. The diagnosis process 230 produces quantitative indication of severity, or state, of mitral valve regurgitation, and it calculates a ventricular (ejection) function determination.

Left Ventricular Dyssynchrony.

This disease is diagnosed by analyzing the flow patterns during the first two analysis phases 220 and 222. During the isovolumic contraction flow phase 220, a prolonged pre-ejection interval is observed. During the next analysis phase, a turbulent or chaotic flow of blood or poor blood flow directionality of blood outflow may be observed. In addition, a redirection "index" is calculated, where:

Index=ECG $Q$ waveform-to-flow redirection time towards outflow/EGG $Q$ waveform-to-aortic valve opening.

The closer this index is to "1", the more efficient is the left ventricle flow redirection and left ventricle systolic performance. Using this information, the diagnosis process 230 indicates further treatment or adjustment of pacing signals.

While the present invention finds primary clinical application in diagnosing diseases of the heart by analyzing blood flow patterns in the left ventricle, as indicated earlier, the method is general and, thus, usable in other clinical applications. For example, imaging blood flow patterns in large blood vessels may reveal pathologies such as aortic valve disease or aortic dissection, to name only a few.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for in vivo imaging of flow pattern of blood in a ventricle of a heart of a subject, the method comprising:
  a) administering particles configured to mix with blood flowing in the ventricle of the heart of the subject to produce a differentiatable acoustic signature;
  b) acquiring, using ultrasonic energy reflected back to a transducer array of an ultrasound imaging system located externally from the subject, images of the ventricle of the heart at a substantially high frame rate selected to track the particles flowing in the ventricle of the heart in successive ones of the ultrasound image frames; and
  c) producing images of the ventricle of the heart indicating at least one of delays of redirected outflow from the ventricle of the heart and delays closing a valve of the heart associated with the ventricle based on the tracking of the particles.

2. The method as recited in claim 1 wherein the ventricle of the heart includes a left ventricle of the subject.

3. The method of claim 1 wherein the substantially high frame rate is at least 200 frames per second.

4. The method of claim 1 wherein step a) includes injecting a contrast agent.

5. The method of claim 4 wherein step a) includes diluting an ultrasound contrast agent.

6. The method of claim 5 wherein the ultrasound contrast agent is diluted to administer one of 10 micrograms/kg of body weight of the subject and 1 mL dissolved in 100 mL/min of saline at a rate of approximately 0.01 to 0.05 mL/min.

7. The method of claim 4 wherein the contrast agent includes a perfluoropropane gas-filled, lipid-stabilized microbubble contrast agent.

8. The method of claim 1 wherein step b) includes acquiring physiological data from the subject temporally correlated with the acquired images.

9. The method of claim 8 wherein the physiological data includes ECG data.

10. The method of claim 1 further comprising step d) overlaying data indicators over the produced images indicating at least one of kinetic energy, momentum, pressure gradient, velocity, acceleration, direction, vorticity, turbulence, and laminarity.

11. The method of claim 1 further comprising step d) diagnosing one of acute ischemia, heart failure, mitral valve regurgitation, and dyssynchrony from the images of the ventricle of the heart indicating the flow characteristics therein based on the tracking of the particles.

12. A method for diagnosing heart disease, the method comprising:
   a) acquiring a series of ultrasound images using an ultrasound transducer array located externally from the subject of a left ventricle of a heart at a substantially high frame rate during a succession of cardiac phases of a cardiac cycle;
   b) producing a series of flow pattern images from the acquired ultrasound images depicting the flow of particles in blood flowing in the left ventricle at successive cardiac phases and indicating at least one of delays of at least one of flow from the left ventricle and valve operation associated with the left ventricle; and
   c) examining the series of flow pattern images during each cardiac phase to detect flow characteristics indicative of a disease.

13. The method of claim 12 wherein step a) includes administering a contrast agent and acquiring the series of ultrasound images after a delay of a number of cardiac cycles.

14. The method of claim 13 wherein the contrast agent is a perfluoropropane gas-filled, lipid-stabilized microbubble contrast agent and is diluted to administer one of 10 micrograms/kg of body weight of a subject being imaged and 1 mL dissolved in 100 mL/min of saline at a rate of approximately 0.01 to 0.05 mL/min.

15. The method of claim 12 wherein the substantially high frame rate is at least 200 frames per second.

16. The method of claim 12 further comprising step d) indicating a presence of a disease based on the examining in step c).

17. The method of claim 16 wherein the disease includes at least one of acute ischemia, heart failure, mitral valve regurgitation, and dyssynchrony from the series of flow pattern images.

18. The method of claim 12 further comprising step d) acquiring physiological data from a subject being imaged temporally correlated with the series of flow pattern images produced in step b).

19. The method of claim 18 wherein the physiological data includes ECG data.

20. The method of claim 12 further comprising step d) overlaying data indicators over the series of flow pattern images indicating at least one of kinetic energy, momentum, pressure gradient, velocity, acceleration, direction, vorticity, circulation, turbulence, and laminarity.

* * * * *

UNITED STATES PATENT AND TRADEMARK OFFICE
CERTIFICATE OF CORRECTION

| | |
|---|---|
| PATENT NO. | : 8,328,724 B2 |
| APPLICATION NO. | : 12/298222 |
| DATED | : December 11, 2012 |
| INVENTOR(S) | : Partho P. Sengupta et al. |

It is certified that error appears in the above-identified patent and that said Letters Patent is hereby corrected as shown below:

In the Specification

Column 1, lines 15-19 "This invention was made with government support under Grant No. HL 70363 and Grant No. HL068573, awarded by the National Institute of Health and, in part, by Grant No. HL 6855 from the National Institute of Health. The United States Government has certain rights in this invention." should read --This invention was made with government support under HL068573 awarded by the National Institutes of Health. The government has certain rights in the invention.--

Signed and Sealed this
Twenty-sixth Day of November, 2013

Margaret A. Focarino
*Commissioner for Patents of the United States Patent and Trademark Office*